United States Patent
Akiva et al.

(10) Patent No.: US 9,818,283 B2
(45) Date of Patent: Nov. 14, 2017

(54) ALERT GENERATION CORRELATING BETWEEN HEAD MOUNTED IMAGING DATA AND EXTERNAL DEVICE

(71) Applicant: Harman International Industries, Incorporated, Stamford, CT (US)

(72) Inventors: Ohad Akiva, Ramat-Gan (IL); Dan Atsmon, Rehovot (IL); Ram Dayan, Tel-Aviv (IL)

(73) Assignee: iOnRoad Technologies Ltd., Ramat-Gan (IL)

( * ) Notice: Subject to any disclaimer, the term of this patent is extended or adjusted under 35 U.S.C. 154(b) by 7 days.

(21) Appl. No.: 14/589,914

(22) Filed: Jan. 5, 2015

(65) Prior Publication Data

US 2015/0194035 A1   Jul. 9, 2015

Related U.S. Application Data

(60) Provisional application No. 61/923,877, filed on Jan. 6, 2014.

(51) Int. Cl.
*G08B 23/00* (2006.01)
*G08B 21/06* (2006.01)
(Continued)

(52) U.S. Cl.
CPC .............. *G08B 21/06* (2013.01); *A61B 5/18* (2013.01); *A61B 5/746* (2013.01); *B60C 9/00* (2013.01);
(Continued)

(58) Field of Classification Search
CPC ........... G08B 21/06; A61B 5/18; A61B 57/46; B60K 28/066; B60C 9/00; G06K 9/00845; H04N 7/183
(Continued)

(56) References Cited

U.S. PATENT DOCUMENTS 6,272,431 B1 * 8/2001 Zamojdo ................ G01C 21/36
                                                              348/115
6,559,770 B1 * 5/2003 Zoerb .................... G08B 21/06
                                                              340/575
(Continued)

FOREIGN PATENT DOCUMENTS

DE          19734307 A1    2/1999
DE     102009005730 A1    7/2010
(Continued)

OTHER PUBLICATIONS

European Patent Office, Extended European Search Report of EP14200139.5, Apr. 28, 2015, Germany, 9 pages.

*Primary Examiner* — Zhen Y Wu
(74) *Attorney, Agent, or Firm* — McCoy Russell LLP (57) ABSTRACT

A method of alerting a vehicle's driver. The method comprises receiving an azimuth value indicating a gazing direction of a head of the driver from a primary device placed on the driver, receiving a vehicle bearing value indicating a vehicle moving direction of the vehicle driven by the driver, calculating an angular difference between the azimuth value and the vehicle bearing value, generating an alert when the angular difference deviates from an angular threshold, and automatically presenting the alert to the driver in response to the angular difference.

19 Claims, 6 Drawing Sheets

(51) Int. Cl.
   *A61B 5/18*   (2006.01)
   *B60K 28/06*  (2006.01)
   *G06K 9/00*   (2006.01)
   *B60C 9/00*   (2006.01)
   *H04N 7/18*   (2006.01)
   *A61B 5/00*   (2006.01)

(52) U.S. Cl.
   CPC ........ B60K 28/066 (2013.01); G06K 9/00845 (2013.01); H04N 7/183 (2013.01)

(58) Field of Classification Search
   USPC ........................................................ 340/575
   See application file for complete search history.

(56) References Cited

U.S. PATENT DOCUMENTS

| | | | | |
|---|---|---|---|---|
| 8,022,831 | B1* | 9/2011 | Wood-Eyre | B60T 7/14 180/272 |
| 8,184,983 | B1* | 5/2012 | Ho | H04B 10/1143 345/156 |
| 2003/0154023 | A1* | 8/2003 | Utsumi | G01C 21/34 701/428 |
| 2004/0178890 | A1* | 9/2004 | Williams | B60Q 9/00 340/425.5 |
| 2006/0214807 | A1* | 9/2006 | Tengshe | G08B 21/06 340/576 |
| 2006/0271286 | A1* | 11/2006 | Rosenberg | G01C 21/3647 701/431 |
| 2007/0008151 | A1* | 1/2007 | Victor | A61B 5/11 340/573.1 |
| 2008/0077320 | A1* | 3/2008 | Loftus | G01C 21/20 701/412 |
| 2008/0165279 | A1 | 7/2008 | Burns et al. | |
| 2009/0192686 | A1* | 7/2009 | Niehsen | B60W 30/17 701/70 |
| 2009/0243880 | A1* | 10/2009 | Kiuchi | G08G 1/166 340/903 |
| 2009/0284552 | A1* | 11/2009 | Larson | G02B 27/01 345/632 |
| 2010/0211307 | A1* | 8/2010 | Geelen | G01C 21/265 701/533 |
| 2011/0144859 | A1* | 6/2011 | Suk | B60W 30/12 701/33.4 |
| 2011/0169625 | A1* | 7/2011 | James | B60Q 9/008 340/439 |
| 2013/0024202 | A1* | 1/2013 | Harris | G06Q 30/00 705/1.1 |
| 2013/0038692 | A1* | 2/2013 | Ohtomo | G05D 1/0038 348/46 |
| 2013/0210406 | A1* | 8/2013 | Vidal | H04W 4/00 455/418 |
| 2014/0098198 | A1* | 4/2014 | Lee | G06F 3/013 348/48 |
| 2014/0111647 | A1* | 4/2014 | Atsmon | H04N 7/185 348/148 |
| 2014/0125474 | A1* | 5/2014 | Gunaratne | G08G 1/163 340/439 |
| 2014/0156183 | A1* | 6/2014 | Windeler | G08G 1/144 701/454 |
| 2014/0210978 | A1* | 7/2014 | Gunaratne | G06K 9/00604 348/77 |
| 2014/0272811 | A1* | 9/2014 | Palan | G07C 5/008 434/66 |
| 2015/0035822 | A1* | 2/2015 | Arsan | G06T 19/006 345/419 |
| 2015/0182759 | A1* | 7/2015 | Baek | A61N 5/0618 359/566 |

FOREIGN PATENT DOCUMENTS

| | | |
|---|---|---|
| EP | 2246831 A1 | 11/2010 |
| WO | 2014170278 A1 | 10/2014 |

* cited by examiner

ALERT GENERATION CORRELATING BETWEEN HEAD MOUNTED IMAGING DATA AND EXTERNAL DEVICE

CROSS REFERENCE TO RELATED APPLICATIONS

This application claims priority to U.S. Provisional Patent Application No. 61/923,877, entitled "ALERT GENERATION CORRELATING BETWEEN HEAD MOUNTED IMAGING DATA AND EXTERNAL DEVICE," filed Jan. 6, 2014, the entire contents of which are hereby incorporated by reference for all purposes.

BACKGROUND

The present disclosure, in some embodiments thereof, relates to vehicle driver detection systems and, more specifically, but not exclusively, to methods and systems of detecting driver inattentiveness, for instance due to drowsiness, and alerting the driver of a vehicle to increase her or his alertness.

One of the most dangerous aspects of long-distance driving is when a driver loses attentiveness, for instance begins dozing off while driving. Drivers, especially when driving alone, have a hard time preventing themselves from beginning to fall asleep which can result in dangerous vehicle crashes. Driver inattentiveness detection systems are currently based on the vehicle's motions. For example, some vehicles' attached systems and onboard circuits monitor jerkiness of a vehicle to estimate inattentiveness of the driver and alert the driver accordingly.

Figure 1:
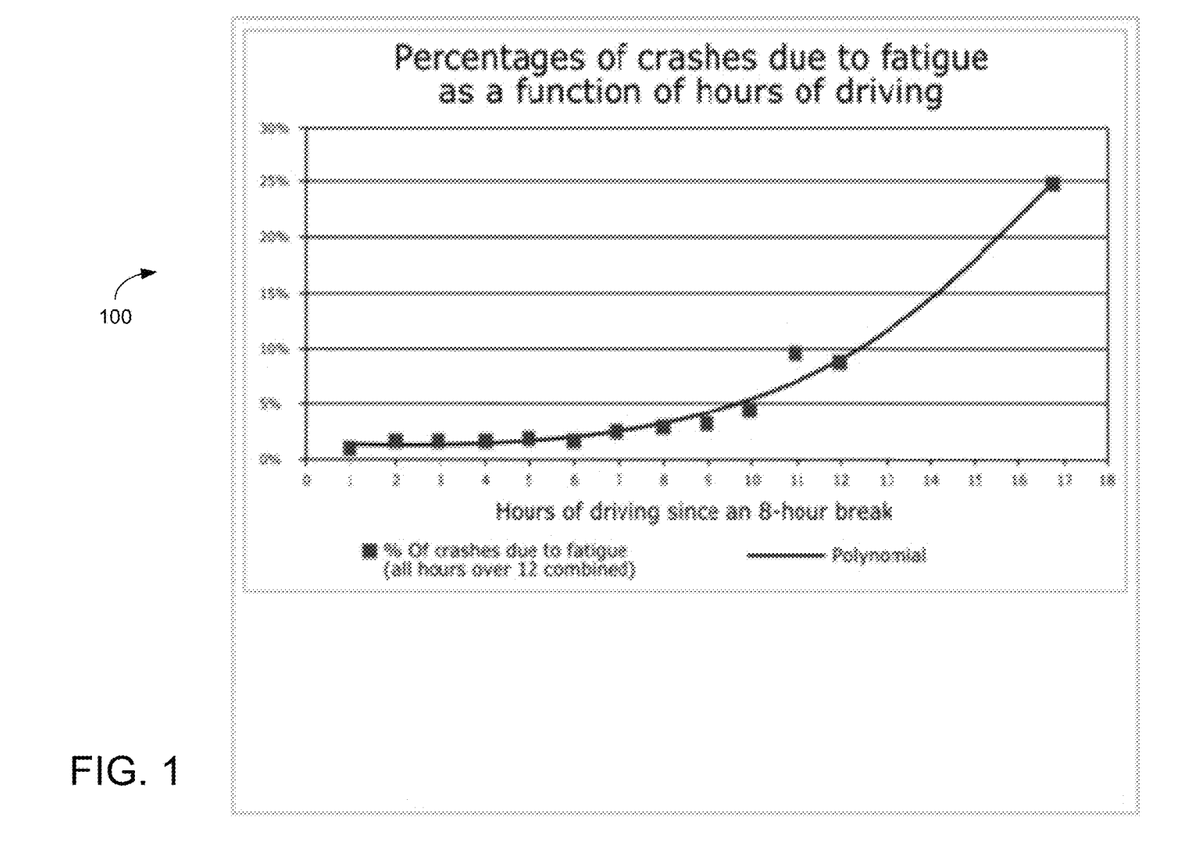
FIG. 1 is a diagram presenting fatigue crash data provided by the Federal Motor Carrier Safety Administration.

Reference is now made to FIG. 1, which is Diagram 100 presenting fatigue crash data provided by the Federal Motor Carrier Safety Administration. Diagram 100 illustrates why the hours of service are important by outlining the relationship between number of hours driven and the percent of crashes related to driver fatigue. As shown, diagram 100 illustrates how crashes due to fatigue increase exponentially with duration of a trip.

If driver inattentiveness is accurately detected, then many types of alerts may be used which are useful for a driver to prevent accidents and wake them up. One dimensional tracking, via steering alone may be inaccurate as it may be confused with the regular swerving of driving, such as moving in and out of lanes frequently.

SUMMARY

According to some embodiments of the present disclosure there is provided a method of alerting a vehicle's driver. The method comprises receiving an azimuth value indicating a gazing direction of a head of the driver from a primary device placed on the driver; receiving a vehicle bearing value indicating a vehicle moving direction of the vehicle driven by the driver; calculating an angular difference between the azimuth value and the vehicle bearing value; generating an alert when the angular difference deviates from an angular threshold; and automatically presenting the alert to the driver in response to the angular difference.

Optionally, the method further comprises receiving a first set of image data, the first set of image data captured by an image capture module coupled to the primary device; receiving a second set of image data, the second set of image data captured by a second device oriented toward the vehicle moving direction; processing the first and second set of image data to determine a comparison result; generating an alert when the angular difference deviates from the angular threshold and the comparison result deviates from an image similarity threshold; and automatically presenting the alert to the driver.

Optionally, the method further comprises receiving a driver activity notification from a secondary device, the driver activity notification indicating whether the driver is interacting with the secondary device; generating an alert when the activity notification indicates that the driver is interacting with the secondary device and the angular difference deviates from an angular threshold; and automatically presenting the alert to the driver.

Optionally, the vehicle bearing value is generated by a geographical positioning system (GPS); and transmitted by a circuit coupled to the vehicle.

Optionally, the vehicle bearing value is generated by a geographical positioning system and transmitted by a mobile device to the primary device placed on the driver.

Optionally, the method further comprises automatically presenting the alert to the driver in response to the angular difference while the angular difference is still present.

According to some embodiments of the present disclosure there is provided a system of alerting a vehicle's driver. Optionally, the system comprises a device with a processor, the device to be placed on the driver's head; a control module which: receives an azimuth value from the device placed on the driver, indicating a gazing direction of a head of the driver; receive a vehicle bearing value indicating a vehicle moving direction of the vehicle driven by the driver; wherein the processor is configured to: calculate an angular difference between the azimuth value and the vehicle bearing value; generate an alert when the angular difference deviates from an angular threshold; and wherein the control module is further configured to automatically present the alert to the driver in response to the angular difference.

Optionally, the system further comprises a first image capture module coupled to the device; and where the control module further: receives a first set of image data captured by the image capture module.

Optionally, the system further comprises a second image capture module coupled to the vehicle and oriented toward the vehicle moving direction; where the control module further: receives a second set of image data captured by the second image capture module; processes the first and second image data to determine a comparison result; generates an alert when the angular difference deviates from the angular threshold and the comparison result deviates from an image similarity threshold; and presents the alert to the driver.

Optionally, the system further comprises receives a plurality of primary device orientation values over a period of time; determines an angular velocity of the head by utilizing the plurality of primary device orientation values; generates an alert when the angular velocity deviates from an angular velocity threshold and the comparison result deviates from the angular threshold; and presents the alert to the driver.

Optionally, the system further comprises an electronic handheld device; wherein the control module presents the alert to the electronic handheld device; and the handheld device sounds a notice as a result of the alert.

Optionally, the system further comprises a mobile phone; wherein the control module presents the alert to the mobile phone; and the mobile phone sounds a notice as a result of the alert.

Optionally, the system further comprises the device is a pair of glasses with an electronic display, and at least one of an accelerometer and a gyro; and wherein the control module presents the alert on the electronic display.

Optionally, the system further comprises the device is a pair of glasses with an electronic display, and GPS; and wherein the control module receives the vehicle bearing value from the GPS.

Optionally, the system further comprises the control module is directly coupled to the vehicle's computer system; and transmits the alert via wireless communication to the device.

According to some embodiments of the present disclosure there is provided a computer readable medium comprising computer executable instructions adapted to perform the method.

According to some embodiments of the present disclosure there is provided a method of alerting a driver of a vehicle comprising: receiving three-dimensional (3D) orientation information from a module on a primary device placed on the driver, the information indicating a gazing direction of the driver's head; determining based on the 3D orientation information when the gazing direction is different from a vehicle moving direction; generating an alert when the gazing direction is determined to be different from the vehicle moving direction; and automatically presenting the alert to the driver when the gazing direction is determined to be different from the vehicle moving direction.

Optionally, the method comprises receiving a first set of image data, the first set of image data captured by an image capture module coupled to the primary device; receiving a second set of image data, the second set of image data captured by a second device oriented toward the vehicle moving direction; processing the first and second set of image data to determine a comparison result; wherein generating further comprises generating an alert when gazing direction is determined to be different from the vehicle moving direction and the comparison result deviates from an image similarity threshold; and automatically presenting the alert to the driver.

Optionally, the method comprises the vehicle gains driving control when the gazing direction is determined to be different from the vehicle moving direction.

Optionally, the method comprises receiving the 3D orientation values multiple times over a period of time; incrementing a count each time the gazing direction is determined to be different from the vehicle moving direction; wherein generating further comprises: generating an alert when the count deviates from a count threshold; and automatically presenting the alert to the driver.

Optionally, the count threshold is determined by a pattern recognition algorithm accounting for the period of time.

Optionally, the method comprises receiving a set of image data, the set of image data captured by an image capture module coupled to the primary device; processing the set of image data to determine an eyes gazing direction result; generating an alert when the gazing direction is determined to be different from the vehicle moving direction and the eyes gazing direction result deviates from an eyes gazing direction threshold; and automatically presenting the alert to the driver.

According to some embodiments of the present disclosure there is provided a method of alerting a driver of a vehicle comprising: receiving a first set of image data, the first set of image data captured by an image capture module coupled to a primary device placed on the driver; receiving a second set of image data, the second set of image data captured by a second device oriented toward the direction the vehicle is heading toward; processing the first and second set of image data to determine a comparison result; wherein generating further comprises generating an alert when the comparison result deviates from an image similarity threshold; and automatically presenting the alert to the driver.

Optionally, the processing of the first set of image data further comprises: comparing a sequence of images in the first set of image data to determine movement of the head relative to the horizon.

Optionally, the azimuth value is determined by a compass of the primary device.

Optionally, the angular threshold is dynamically modified based on data received from the secondary device.

Optionally, the vehicle bearing value is generated by a compass; and transmitted by a circuit coupled to the vehicle.

Optionally, the processing of the first set of image data further comprises: comparing a sequence of images in the first set of image data to determine movement of the head relative to the horizon.

Optionally, presenting the alert further comprises: providing a suggestion to the driver to navigate to a rest location, the rest location including at least one of: a restaurant, coffee shop, rest stop and parking lot.

Unless otherwise defined, all technical and/or scientific terms used herein have the same meaning as commonly understood by one of ordinary skill in the art to which the disclosure pertains. Although methods and materials similar or equivalent to those described herein can be used in the practice or testing of embodiments of the disclosure, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the disclosure are herein described, by way of example only, with reference to the accompanying drawings. With specific reference now to the drawings in detail, it is stressed that the particulars shown are by way of example and for purposes of illustrative discussion of embodiments of the disclosure. In this regard, the description taken with the drawings makes apparent to those skilled in the art how embodiments of the disclosure may be practiced.

In the drawings.

DETAILED DESCRIPTION

The present disclosure, in some embodiments thereof, relates to vehicle driver detection systems and, more specifically, but not exclusively, to methods and systems of detecting driver inattentiveness and alerting the driver of a vehicle while dozing off.

Some embodiments of the disclosure enable vehicle driver inattentive event detection correlating between head movements of a driver and the direction the vehicle is heading toward. Head movements may be measured to indicate yaw, roll, pitch and/or tilt. Typical inattentive detection systems are based on an analysis of the motion of a vehicle. Correlating between the head motion of the driver and outputs of additional sensors, such as a camera, an accelerometer, and a geographical positioning system (GPS), provides a more accurate detection of inattentive events, reducing false positive alerts and false negative inattentive event estimation. Some embodiments of the disclosure enable head mounted display devices worn by the driver to obtain an azimuth value indicating the gazing direction of the driver's head, receive a vehicle bearing value indicating the direction of the vehicle being driven, by a GPS, mobile phone/Smartphone and/or In-Vehicle Infotainment (IVI) system, and calculate the angular difference between the two values. Optionally, the head mounted display device and/or the glasses with an electronic display, presents an alert to the driver when the angular difference deviates from an angular threshold. Optionally, the vehicle bearing value is generated by a GPS and transmitted by the IVI/mobile device and/or a circuit coupled to the vehicle. Optionally the vehicle bearing is generated by a GPS system and transmitted by a mobile device to the head mounted display. Optionally, the alert is automatically presented to the driver in response to the angular difference while the angular difference is still present.

Optionally, the head mounted display device comprises an accelerometer to detect motion in the gazing direction of the head. Optionally, the vehicle and/or an infotainment system have a geographical positioning system (GPS) that transmits the vehicle bearing used to indicate the direction the vehicle is heading toward. Optionally, the GPS, accelerometer, and azimuth reading all take place in the head mounted display. Optionally, the IVI determines the gazing direction and direction the vehicle is heading toward alone by receiving and/or acquiring GPS, camera and/or accelerometer information. Optionally, the IVI receives a compass reading from the head mounted display, and compares it to the GPS reading to determine the angular difference. Optionally, the GPS, accelerometer, and azimuth reading and comparison all take place in a handheld device such as a mobile phone. Optionally, the head mounted display device or method used on the head mounted display includes a more robust verification than azimuth and bearing comparison alone, including image comparison between images taken by a camera on the vehicle and one taken by a camera on the glasses in conjunction with the azimuth and bearing comparison.

In some embodiments, 3D orientation information is received from a module on a primary device which is placed on the driver. The 3D information may indicate the gazing direction of the driver's head. The 3D information may be generated by an accelerometer and/or gyro. The 3D information may indicate the yaw, roll, pitch and/or tilt of the head. Optionally, an alert is generated when the 3D information indicates that the gazing is downward and/or moving downward.

The benefits of the system in the present disclosure include more robust and accurate detection of inattentiveness due to the multiple sense inputs. Former systems only detected vehicle motion and jerkiness. Some embodiments of the present disclosure enable driver attentiveness detection by sensing the state of the driver themselves. Sensing the state of the driver includes head motions and/or eye state detection such as when the driver's eyes are closed. Some embodiments of the present disclosure have more robust detection by many combinations of any of the detected senses including gazing direction images, eye images, GPS bearings and gazing direction changes.

Before explaining at least one embodiment of the disclosure in detail, it is to be understood that the disclosure is not necessarily limited in its application to the details of construction and the arrangement of the components and/or methods set forth in the following description and/or illustrated in the drawings and/or the Examples. The disclosure is capable of other embodiments or of being practiced or carried out in various ways.

As will be appreciated by one skilled in the art, aspects of the present disclosure may be embodied as a system, method, or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 2A:
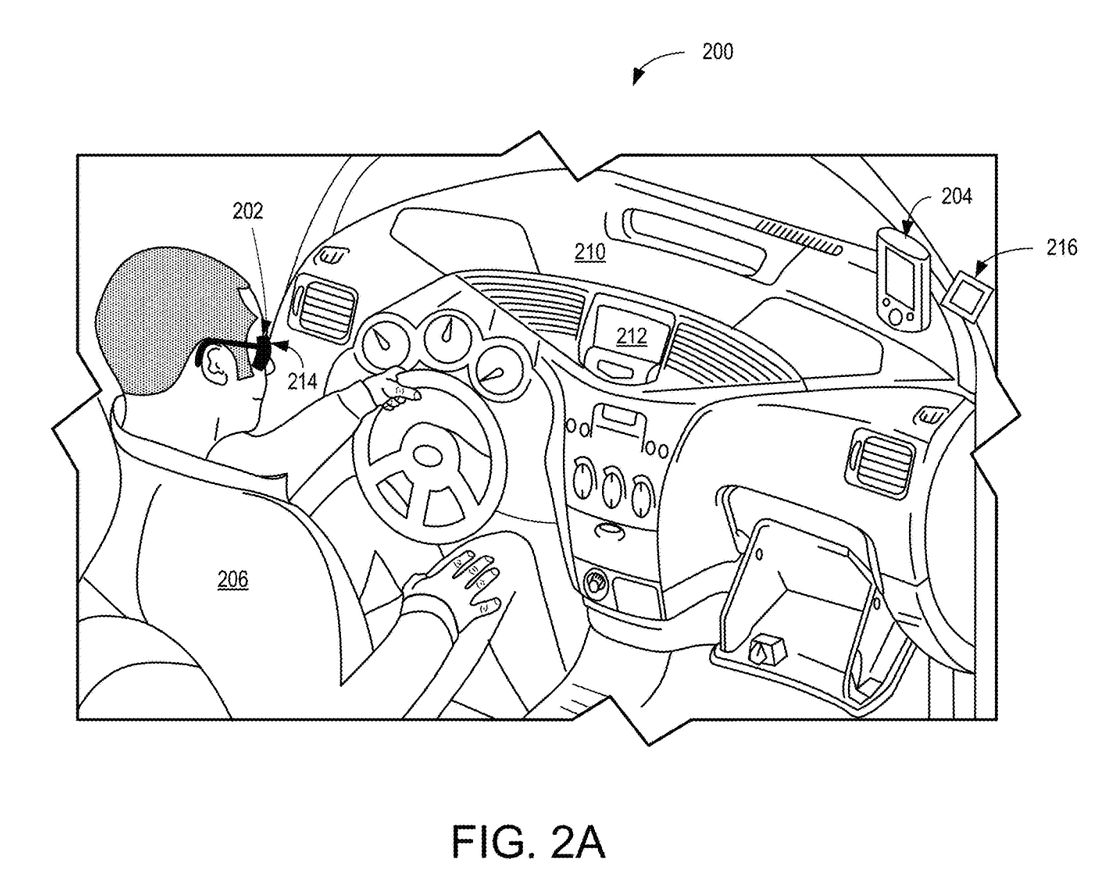
FIG. 2A is a schematic illustration of a system, for detecting a vehicle driver's inattentiveness according to some embodiments of the present disclosure.

Reference is now made to FIG. 2A, which is a schematic illustration of a System 200, for detecting a vehicle driver's inattentiveness according to some embodiments of the present disclosure. A Wearable Computing Device 202 may connect to External Device 204 through a wired and/or wireless method. For example, Wearable Computing Device 202 connects to External Device 204 through Blue Tooth (BT), 2.4 Gigahertz wireless connectivity and/or radio frequency wireless connectivity. External Device 204 may be a tablet/computer/smartphone/mobile phone which is separated from the vehicle. Wearable Computing Device 202 may connect to Vehicle Infotainment System 212 which is coupled to the vehicle itself and/or a circuit in the vehicle. Vehicle Infotainment System 212 may be an IVI. Optionally, IVI includes systems that are attached and/or communicate directly with a vehicle's computer system. External Device 204 may be part of Dashboard 210 and/or sit on top of Dashboard 210.

Optionally Wearable Computing Device 202 is a primary device which is placed on the driver and has a compass and/or accelerations sensor to detect motion and/or gazing direction of Driver 206's head. The compass, and/or accelerations sensors may indicate the yaw, roll, pitch and/or tilt of the head. Optionally, Wearable Computing Device 202 has a camera and/or image capture device such as Image Capture Module 1 214 to take pictures from Driver 206's perspective. Optionally, External Device 204 has a camera and/or image capture device, such as Image Capture Module 2 216, to take pictures from the vehicle's perspective. Optionally, external device's camera is mounted to the vehicle's dashboard, part of the vehicle itself such as in the headlight, above a bumper, and/or part of a mobile phone. Optionally, Wearable Computing Device 202 and/or External Device 204 have any of the following to enable communication between said devices: a screen and/or monitor, a microphone and/or audio detection system, a GPS, a processor and/or integrated circuit to process the images and the communication between the devices.

Figure 2B:
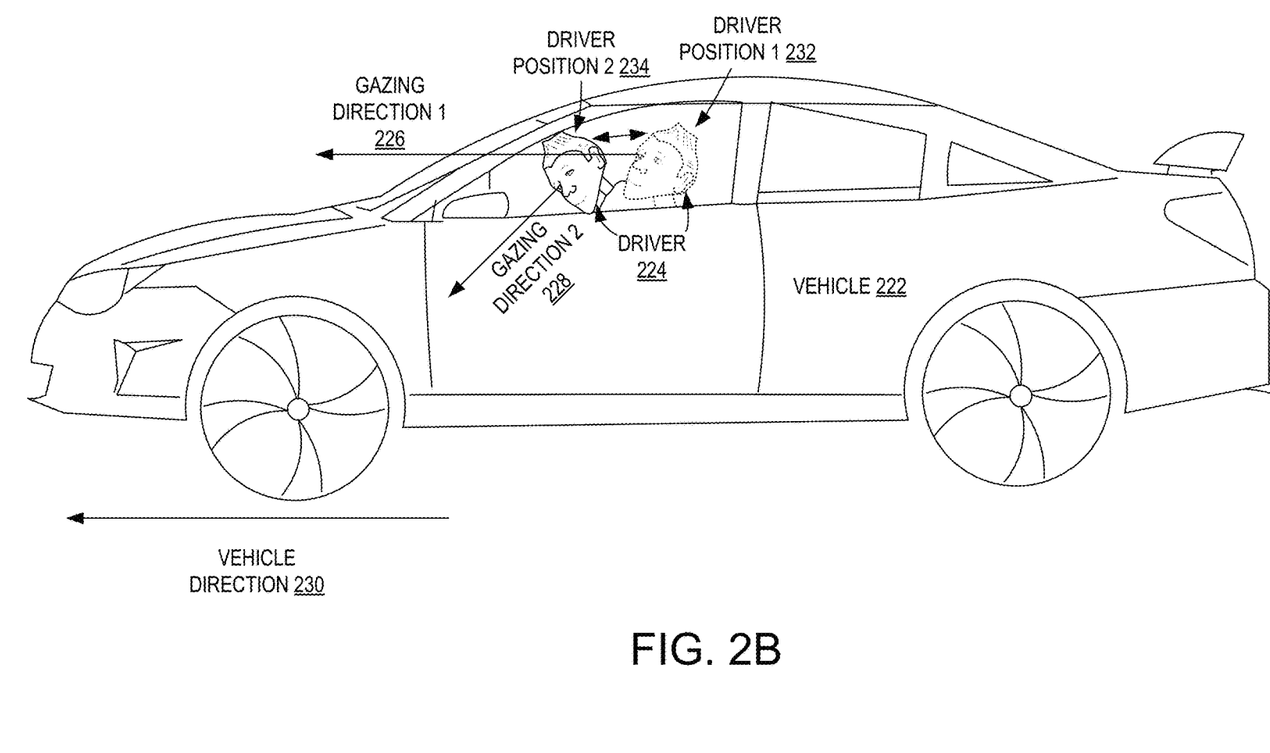
FIG. 2B is a schematic illustration of angular measurements according to some embodiments of the present disclosure.
Figure 3:
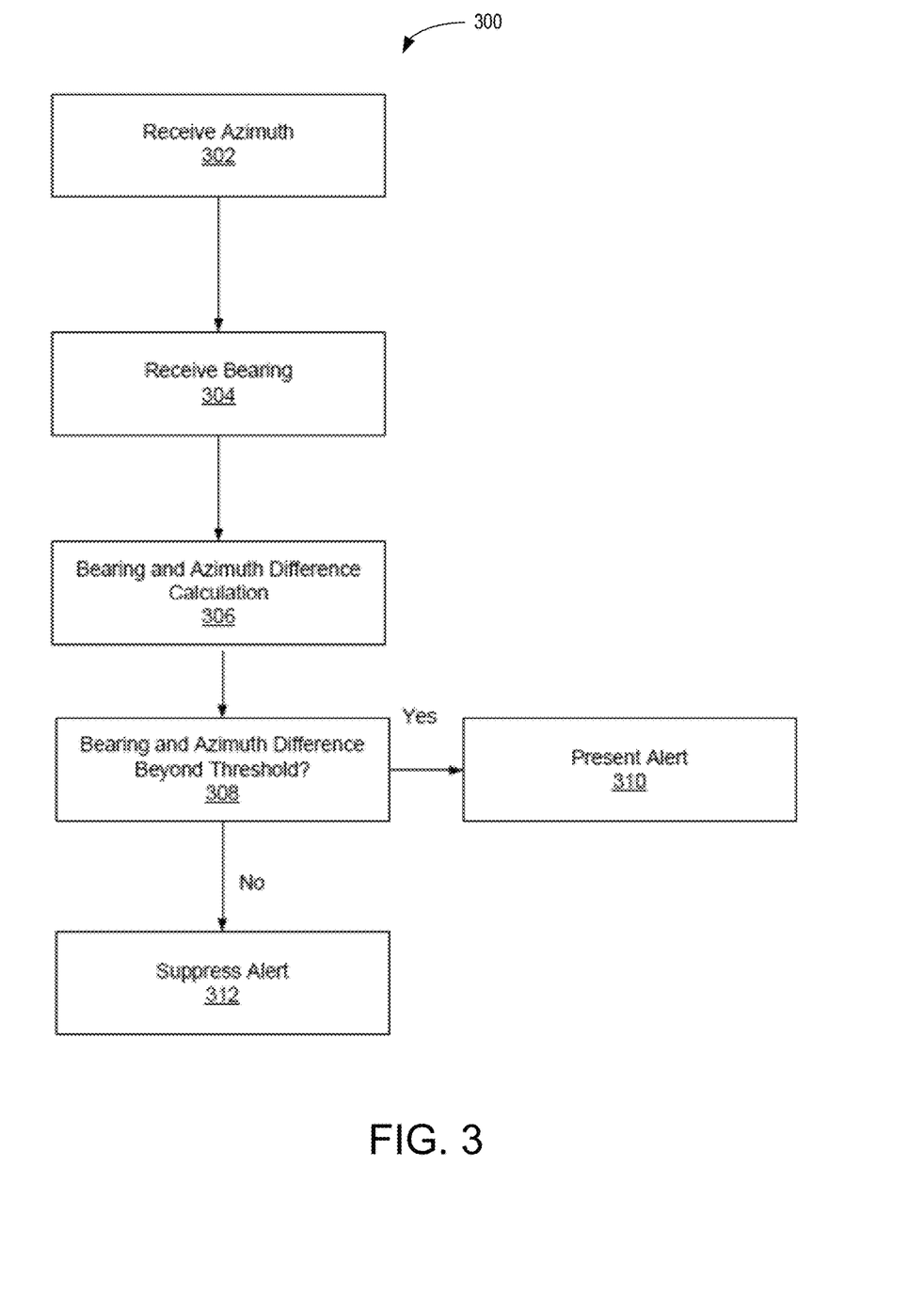
FIG. 3 is a flowchart of a method of driver inattentiveness detection based on azimuth and bearing according to some embodiments of the present disclosure.

Reference is now made to FIG. 2B which is a schematic illustration of System 220 demonstrating angular measurements according to some embodiments of the present disclosure. Driver 224 of Vehicle 222 may be in Driver Position 1 232 while attentive. While in Driver Position 1 232, the driver may have Gazing Direction 1 226. When driver is losing attentiveness, for example, he may be nodding off and fall to Driver Position 2 234. Moving from Gazing Direction 1 226 to Gazing Direction 2 228 may be detected by 3D orientation readings from an accelerometer, a gyro, and/or 3D orientation values of Wearable Computing Device 202 when driver is in Driver Position 2 234. Vehicle Direction 230 may represent the direction the vehicle is heading toward and is determined by a GPS, mobile phone and/or IVI system. Reference is now made to FIG. 3, which is Flowchart 300 presenting a method of driver inattentiveness detection based on azimuth and bearing readings according to some embodiments of the present disclosure. Flowchart 300 presents a method which details head gazing direction of a driver and compares it to the detected direction vehicle is heading toward. This is useful to sense when a driver is nodding off and her head is facing the ground. Flowchart 300 may also be useful to detect when a driver is looking back at other passengers or outside scenery and not in the viewing direction. Angular velocity of the head motion may be accounted for. For example, a plurality of 3D orientation values are received over a period of time and an angular velocity of the head is determined. Optionally, different angular thresholds and angular velocity thresholds and/or ranges are used to prevent inaccurate detection. For example, a wide range of thresholds are used for a vehicle stopped such as at a traffic light or parked. Optionally, images are taken of the drivers pupils to determine when his eyes are closed. Optionally, the image data is processed to determine an eyes open result when the drivers' eyes are open. Optionally, when there is an eyes open result that indicates that the eyes are closed and the angular difference deviates from the angular threshold an alert is generated. Optionally, a wide range of angular velocity and/or angular thresholds are used when a driver is stuck in heavy traffic. In 302, an azimuth value is received from a primary device which is placed on the driver. In some embodiments, Wearable Computing Device 202 and/or glasses which have computing capabilities are used as the primary device. The azimuth value may indicate the gazing direction of the driver's head. Optionally, the azimuth value is determined from a compass on the Wearable Computing Device 202, and/or image processing. Optionally, the wearable computing device receives 3D orientation information from an accelerometer, and/or gyro which indicates the orientation and/or motion of the driver's head. The compass, and/or accelerations sensors may indicate the yaw, roll, pitch and/or tilt of the head. Optionally, the Wearable Computing Device 202, and/or External Device 204 receives the azimuth value and proceeds with the rest of the method in Flowchart 300. Optionally, the wearable computing device processes a set of image data taken of the eyes, to determine an eyes gazing direction result.

In 304, a vehicle bearing value is received which indicates the direction the vehicle is heading toward. For example, in 304 the wearable computing device calculates the GPS and/or receive GPS from the IVI/mobile phone. Optionally, the GPS is on the wearable device and/or on the external device. In 304 vehicle bearing indicates the direction the vehicle is heading toward by the driver. Optionally, the IVI system/mobile phone receives and/or calculates the bearing and/or GPS information. Optionally images are taken from the external device and/or wearable computing device and the angular difference is computed based on the difference in the images. Optionally images are taken from the Image Capture Module 1 214 and/or Image Capture Module 2 216 and the angular difference is computed based on the difference in the images.

In 306, the angular difference between the azimuth value and the vehicle bearing value may be calculated. The azimuth value should indicate the horizontal angle of the driver's head on a plane parallel to the ground, so when a driver is facing left or right, the angular difference is greater than 5° or 10°, for example. In 308, the wearable computing device may determine when the bearing and azimuth difference deviates from a threshold value. Optionally, the threshold may be 1°, 2°, 5°, 30° and/or any value intermediate or greater. Optionally, the wearable computing device determines when the eyes gazing direction result deviates from an eyes gazing direction threshold.

In 310, an alert may be generated and presented to the driver when the angular difference is above and/or deviates from the threshold. Optionally, the alert is suppressed in 312 when the angular difference does not deviate from the threshold. Optionally, the alert is done through the IVI, the wearable computing device, a mobile device, and/or a mobile phone. Advanced Driver Assistance Systems (ADAS) may be used and/or include IVI, as well as lane departure warning systems, lane change assistance, collision avoidance systems and intelligent speed adaptation. Optionally, the alert is a sounded collision alert, off-road alert and/or headway alert through an ADAS. Optionally, the alert is an audio, visual, and/or vibration alert. Optionally the alert suggests to the driver a route to a nearby rest location, coffee shop, diner and/or the like. Optionally the horizontal angle deviation is checked and/or tilt angle deviation. Different angles may indicate the driver looking to his right or left, and/or at diagonals. Optionally, the vehicle is on an incline or decline.

Optionally driving patterns are tracked for data accumulation. For example, insurance carriers who want to use the data to predict and/or analyze the results. Optionally, no alert is generated or sent. Optionally, the wearable computing device, IVI and/or mobile phone accumulate driver use data for storage or transmission to another source.

Figure 4:
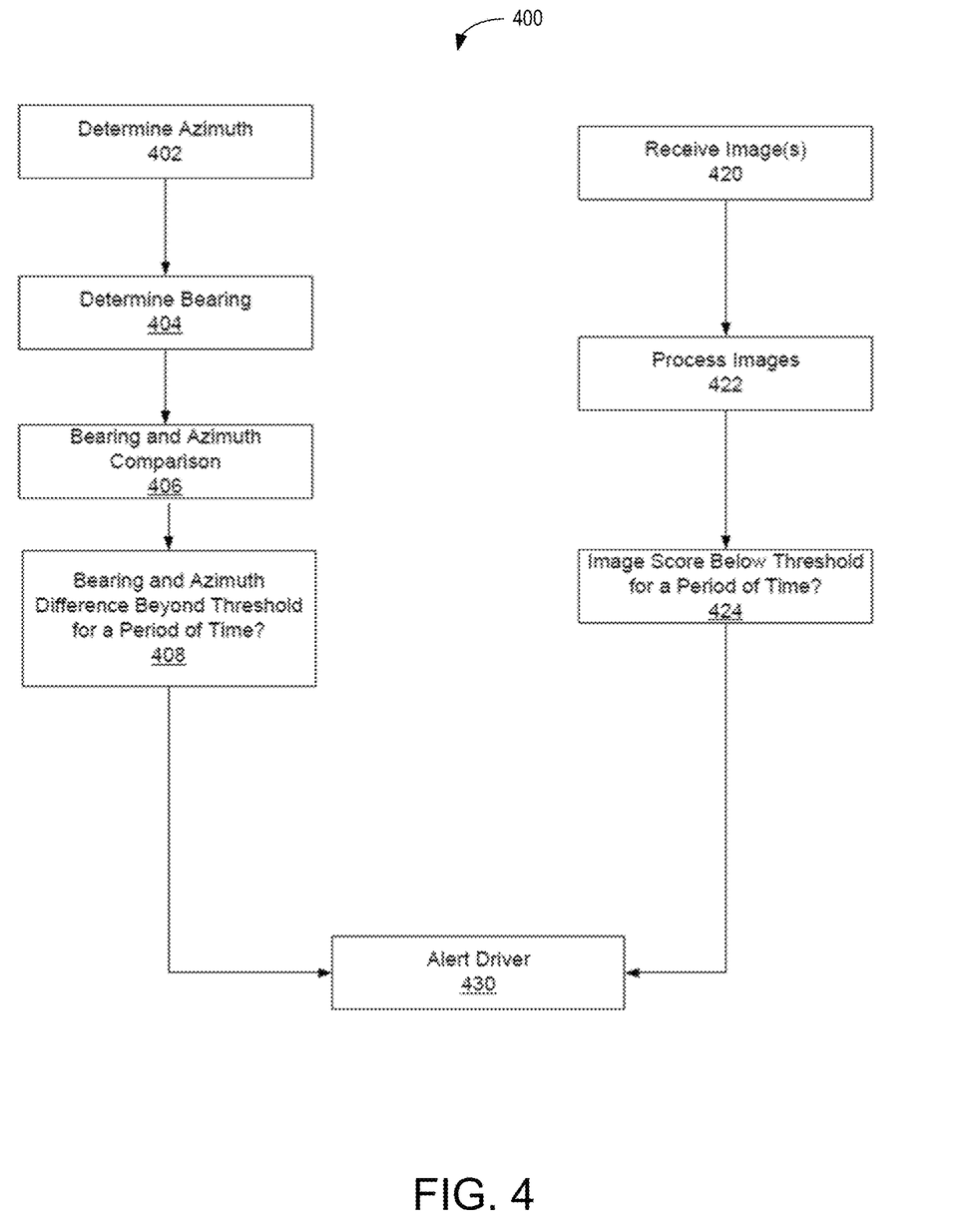
FIG. 4 is a flowchart of a method of driver inattentiveness detection based on azimuth readings and image comparison according to some embodiments of the present disclosure.

Reference is now made to FIG. 4, which is Flowchart 400 presenting a method of driver inattentiveness detection based on azimuth readings and image comparison according to some embodiments of the present disclosure. Flowchart 400 is an exemplary embodiment of a more robust method shown in FIG. 3, with a secondary indication of inattentiveness drawn from image capture modules. In 402, an azimuth value is received from a primary device which is placed on the driver. The azimuth value may indicate the horizontal orientation of the driver's head. Optionally, the azimuth value is determined from a compass on the Wearable Computing Device 202.

In 404, a vehicle bearing value is received which indicates the direction the vehicle is heading toward. For example, in 404 the wearable computing device calculates the GPS and/or receive GPS from the IVI/mobile phone. In 406, the angular difference between the azimuth value and the vehicle bearing value may be calculated. The azimuth value should indicate the angle of the driver's head, so when a driver is facing left or right the angular difference is greater than 5° or 10°, for example. In 408, the wearable computing device may determine when the bearing and azimuth difference is above a threshold value for a period of time. The period of time may be 1, 2, 5, 10 seconds, and/or any intermediate or longer period of time. Timed detection can ensure higher quality. For example, when a driver is looking at something on the road, or at the back seat toward another passenger, longer periods of time of detection are more likely to indicate a driver facing down.

In 420-424, the wearable computing device or external device receive and process images used to determine when the driver is looking in various directions. In 420, the wearable computing device receives a first set of image data which was captured by an image capture module attached to the wearable computing device. The image capture module may be a camera, a video camera and/or the like. In 420, the wearable computing device may also receive a second set of image data from a second image capture module which is fixed toward the direction the vehicle is heading toward. Optionally, the second image capture module is attached to the external device, the dashboard of the vehicle, and/or to the front of the vehicle.

In 422 the wearable computing device may perform an image processing mechanism on the first and second image data sets to determine a comparison result indicating when the driver is facing the road. Image processing techniques may include those include in US Patent Publication 2008/0165279, herein incorporated in its entirety. For example, when the driver is inattentive and falling asleep, the images perspectives are highly dissimilar, for example more than 40% or 50%, because the image captured by the first device, facing upward, downward or to the sides, is different from that of the second capture device which captures the road ahead. For example, when a driver is looking ahead most of the elements in the picture taken from his perspective and the image taken by the perspective of the car/IVI/mobile phone will be the same. For example, looking ahead, a driver and the car will see the same cars ahead, scenery (trees, buildings etc.) and oncoming traffic. Optionally, the images may be taken at specific times, and/or after certain durations of a trip. Optionally, the image processing mechanism is image subtraction, use of correlation algorithms, image registrations, point mapping registrations and/or the like. Optionally, image processing mechanism assigns a score as a result of the mechanism performed. Optionally, image processing compares a sequence of images in a set of image data to determine movement of the head relative to the horizon.

In 424 the score may be compared to a threshold for a period of time. The period of time may be 1, 2, 5, 10 minutes, and/or any intermediate or longer period. In 430, the driver may be alerted when 408 and 424's conditions are satisfied. For example, when the bearing and azimuth have an angular difference beyond a threshold and for a threshold period of time, and the image processing score is below a threshold, for a threshold period of time, then the driver is alerted. Optionally, a score is assigned to the angular difference between the azimuth and bearing, and combined with the image score to create a combined score. Optionally, each score element of the combined score, (image score and/or angular difference) is weighed more or less relative to each other, For example, the image processing score is weighed more than bearing and azimuth difference score and/or vice versa. Optionally, the weighting is assigned based on the accuracy of a signal. For example, when the GPS signal is low, then a lower weight is assigned to the azimuth and bearing difference.

Some embodiments of the present disclosure include variations which enable more accurate inattentiveness determinations. More robust implementations may be used at 308-312 and/or 430 to alert and/or suppress alerts for the driver. Optionally, indications from third devices, such as mobile phones and/or IVI are used to suppress alerts. For example, when a driver is pushing buttons and/or talking on her mobile phone, the phone communicates with wearable computing device to indicate the driver is awake. Optionally, the image capture devices are faced toward the driver's eyes and track drivers' eyes. For example, a camera is faced inwards, captures and detects when a driver is closing her eyes. Optionally, alerts are suppressed when the camera captures and detects that the driver is awake and not sleeping. Optionally, the image processing mechanism determines the driver is inattentive when no pupils present, or the drivers eyes are closed done via color and/or contrast recognition. Optionally, when the azimuth of the head and/or the pupil image processing indicate that the driver is attentive, the alert is stopped. For example, the image processing determines that the drivers eyes are fully open and/or the azimuth and bearing comparison indicates that the drivers head is all the way forward. Optionally, upon continuous eyes closing, head falling and/or vehicle jerking detection, the threshold is lowered and the system is more likely to alert.

Optionally, angular velocity is detected for head motion by calculating 3D orientation over time. Optionally, head motion is tracked. Optionally, when angular change and/or angular velocity changes deviate from a threshold, the event is logged as a head drop event. Optionally, when the velocity and/or angular change are in the opposite direction, an event is logged as a head lift event. A head drop followed by a head lift may contribute to the scores mentioned, and/or generate an alert for the driver. Optionally, lane drifts and/or changes are detected and factored into the accuracy of the azimuth-bearing calculations and image processing mechanisms. Optionally, lane drifts and/or changes are detected through an ADAS system. Optionally, the thresholds and/or threshold ranges are changed dynamically and/or statically. For example, the threshold is changed based on the driving location such as city, hillside, and/or countryside. Optionally, GPS information received indicates the type of location. Optionally, multiple passengers are detected and accounted for in determining the threshold. For example, when the driver is talking to a passenger and/or turning their head, the IVI/mobile phone and/or image processing mechanisms notify that there is another passenger and change the threshold.

Optionally, known algorithms and/or statistical methods are used to enhance the accuracy of the alert detection. Optionally, pattern recognition, neural networks, and/or machine learning are used as statistical methods. Optionally, driver specific behavior is tracked which utilizes a database including driving duration, distance, speed, head drops/lifts, lane shifting, and/or road departures. Optionally, each event is tracked with timestamps, and data analysis done over time. Optionally, each behavior is given a score, and/or scored over a window of time. For example, data is compared during hour 8 of driving versus hour 2 of driving to see when large perturbations exist. Optionally, the window of time is 30 seconds, 2 minutes, 5 minutes, 1 hour and/or any number intermediate of larger. Optionally, the window of time is based on the time of day, and/or the duration of the drive. Optionally, a count is incremented each time a respective angular difference deviates from the angular threshold and an alert is generated when the count deviates from a count threshold. Optionally, the count threshold is determined by a pattern recognition algorithm and accounts for the period of time.

Optionally, a count is incremented each time an angular difference deviates from the angular threshold. Optionally, an alert is generated when the count deviates from a count threshold which is determined by a pattern recognition algorithm which accounts for the period of time in consideration.

Data from FIG. 1 may be used in weighing factors and/or scoring. For example, certain criteria may be weighed more heavily after 8 and/or 9 hours. For example, head drops and head lifts may begin getting scored after 8 hours. For example, the time period window may become much shorter after several hours of a drive. For example, the time period is 5 minutes during the first 6 hours, and then 30 seconds beginning on the $6^{th}$ hour.

Figure 5:
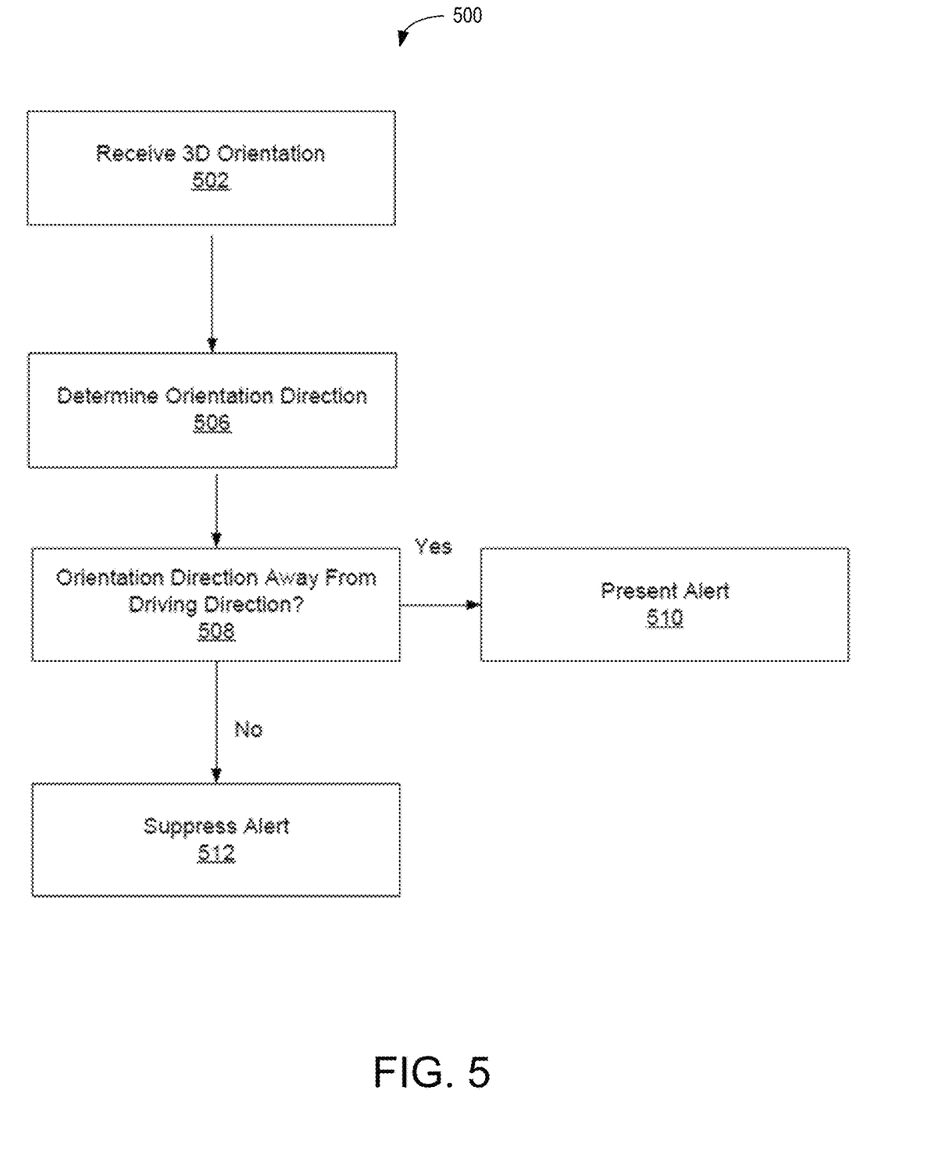
FIG. 5 is a flowchart of a method of driver inattentiveness detection based on three-dimensional (3D) orientation according to some embodiments of the present disclosure.

Reference is now made to FIG. 5 which is a Flowchart 400 of a method of driver inattentiveness detection based on (3D) orientation according to some embodiments of the present disclosure. In 502 a 3D orientation is received from a primary device which is placed on the driver. In 506, the primary device, IVI and/or mobile phone may determine the orientation direction of the head. The orientation may be up, down, left, right and/or at any angle. In 508, the primary device may determine when the orientation direction is down, and/or the driver is falling asleep. In 510-512 an alert is either generated and presented when the head is determined to be facing down or suppressed when not. Optionally, 402-408 are used with 502-512 to increase accuracy over using 402-408 alone. The 3D information may indicate the yaw, roll, pitch and/or tilt of the head.

The methods as described above are used in the fabrication of integrated circuit chips.

The flowchart and block diagrams in the Figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant systems and methods will be developed and the scope of the term GPS, accelerometer, glasses and smartphone is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the disclosure may include a plurality of "optional" features unless such features conflict.

Throughout this application, various embodiments of this disclosure may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination or as suitable in any other described embodiment of the disclosure. Certain features described in the context of various embodiments are not to be considered essential features of those embodiments, unless the embodiment is inoperative without those elements.

Although the disclosure has been described in conjunction with specific embodiments thereof, it is evident that many alternatives, modifications, and variations will be apparent to those skilled in the art. Accordingly, it is intended to embrace all such alternatives, modifications and variations that fall within the spirit and broad scope of the appended claims. For example, unless otherwise noted, one or more of the described methods may be performed by a suitable device and/or combination of devices, such as vehicle infotainment system 212, wearable computing device 202, external device 204, etc., as described with reference to FIG. 2A in combination with one or more sensors and/or actuators. The methods may be performed by executing stored instructions with one or more logic devices (e.g., processors) in combination with one or more additional hardware elements, such as storage devices, memory, hardware network interfaces/antennas, clock circuits, sensors, actuators, etc. The described methods and associated actions may also be performed in various orders in addition to the order described in this application, in parallel, and/or simultaneously.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

The invention claimed is:

1. A method of alerting a vehicle's driver, comprising:
with a processor:
measuring head movements of the driver by a wearable mount placed on the driver;
calculating an azimuth value indicating a horizontal orientation facing direction of a head of said driver;
receiving a vehicle bearing value indicating a current vehicle moving direction of a vehicle driven by the driver;
calculating an angular difference between the azimuth value and the vehicle bearing value;
receiving a first set of image data, the first set of image data captured by a first image capture module coupled to the wearable mount and directing outwardly from the driver to capture a driver's perspective;
receiving a second set of image data, the second set of image data captured by a second image capture module mounted on the vehicle and oriented toward the current vehicle moving direction to capture a vehicle's perspective;

processing the first and second sets of image data to determine a comparison result, the comparison result determined according to image similarity between the first and second sets of image data;

generating an alert according to said comparison result and when the angular difference deviates from an angular threshold, said angular threshold selected from a plurality of predefined angular thresholds according to a traffic condition; and automatically presenting the alert via an alert module to the driver.

2. The method of claim 1,
wherein said generating further comprises generating an alert when the angular difference deviates from the angular threshold and the comparison result deviates from an image similarity threshold; and
automatically presenting the alert to the driver.

3. The method of claim 1, wherein the angular threshold is dynamically modified based on the first and second sets of image data received.

4. The method of claim 1, wherein the vehicle bearing value is generated by a geographical positioning system (GPS); and
wherein the vehicle bearing value is transmitted by one or more of a circuit coupled to the vehicle and a mobile device to the wearable mount placed on the driver.

5. The method of claim 1, further comprising:
automatically presenting the alert to the driver in response to the angular difference while the angular difference is still present.

6. The method of claim 1, wherein said automatically presenting the alert further comprises providing a suggestion to said driver to navigate to a rest location, said rest location including at least one of a restaurant, a coffee shop, a rest stop, and a parking lot.

7. A system of alerting a driver of a vehicle, comprising:
a wearable mount comprising a processor, said wearable mount configured to be placed on a head of said driver measuring head movements of said driver and calculating an azimuth value indicating a horizontal orientation facing direction of the head of said driver;
a first image sensor coupled to said wearable mount, the first image sensor directing outwardly from said driver to capture a driver's perspective;
a second image sensor coupled to the vehicle and oriented toward a vehicle moving direction to capture a vehicle's perspective;
wherein said processor executes code instructions comprising:
code instructions for receiving said azimuth value from said wearable mount placed on the driver;
code instructions for receiving a vehicle bearing value indicating a current vehicle moving direction of the vehicle driven by the driver;
code instructions for calculating an angular difference between the azimuth value and the vehicle bearing value;
code instructions for receiving a first set of image data captured by said first image sensor;
code instructions for receiving a second set of image data captured by said second image sensor;
code instructions for processing the first and second sets of image data to determine a comparison result, the comparison result determined according to image similarity between said first and second sets of image data;
code instructions for generating an alert according to said comparison result and when the angular difference deviates from an angular threshold, said angular threshold selected from a plurality of predefined angular thresholds according to a traffic condition; and
code instructions for automatically presenting the alert via an alert module to the driver.

8. The system of claim 7, further comprising:
code instructions for generating an alert when the angular difference deviates from the angular threshold and the comparison result deviates from an image similarity threshold; and
code instructions for presenting the alert to the driver.

9. The system of claim 7, wherein said code instructions further comprise:
code instructions for receiving a plurality of wearable mount orientation values over a period of time;
code instructions for determining an angular velocity of the head of said driver by utilizing the plurality of wearable mount orientation values;
code instructions for generating an alert when the angular velocity deviates from an angular velocity threshold and the comparison result deviates from the angular threshold; and
code instructions for presenting the alert to the driver.

10. The system of claim 9, wherein said angular velocity threshold and said angular threshold are selected according to a traffic heaviness condition.

11. The system of claim 7, further comprising:
a mobile phone;
wherein said code instructions further comprise code instructions for presenting the alert to the mobile phone; and
the mobile phone sounds a notice as a result of the alert.

12. The system of claim 7, wherein:
said wearable mount is a pair of glasses with an electronic display, and at least one of an accelerometer and a gyro; and
wherein said code instructions further comprise code instructions for presenting the alert on the electronic display.

13. The system of claim 7, wherein:
said wearable mount is a pair of glasses with an electronic display and a GPS; and
wherein said code instructions further comprise code instructions for receiving the vehicle bearing value from the GPS.

14. The system of claim 7, wherein:
the processor is directly coupled to a vehicle's computer system; and
said code instructions further comprising code instructions for transmitting the alert via wireless communication to said wearable mount.

15. A method of alerting a driver of a vehicle comprising:
with a processor:
receiving three-dimensional orientation information from a module on a wearable mount placed on the driver, the information indicating a horizontal orientation facing direction of a head of the driver;
determining based on the orientation information when the horizontal orientation facing direction is different from a current vehicle moving direction;

receiving a first set of image data, the first set of image data captured by a first image capture module coupled to the wearable mount and directing outwardly from said driver to capture a driver's perspective;

receiving a second set of image data, the second set of image data captured by a second image capture module oriented toward the current vehicle moving direction to capture a vehicle's perspective;

processing the first and second sets of image data to determine a comparison result, the comparison result determined according to image similarity between said first and second sets of image data;

generating an alert according to said comparison result and when the horizontal orientation facing direction is determined to be different from the current vehicle moving direction; and automatically presenting the alert via an alert module to the driver.

16. The method of claim 15, wherein generating further comprises generating an alert when the horizontal orientation facing direction is determined to be different from the current vehicle moving direction and the comparison result deviates from an image similarity threshold; and automatically presenting the alert to the driver.

17. The method of claim 15, wherein:

the vehicle gains driving control when the horizontal orientation facing direction is determined to be different from the current vehicle moving direction.

18. The method of claim 15, further comprising:

receiving the orientation information multiple times over a period of time;

incrementing a count each time the horizontal orientation facing direction is determined to be different from the current vehicle moving direction;

wherein generating further comprises generating an alert when the count deviates from a count threshold, the count threshold being determined by a pattern recognition algorithm accounting for the period of time; and automatically presenting the alert to the driver.

19. The method of claim 15, further comprising:

receiving a third set of image data, the set of image data captured by the first image capture module coupled to the wearable mount;

processing the third set of image data to determine an eyes gazing direction result;

generating an alert when the horizontal orientation facing direction is determined to be different from the current vehicle moving direction and the eyes gazing direction result deviates from an eyes gazing direction threshold; and automatically presenting the alert to the driver.

* * * * *

UNITED STATES PATENT AND TRADEMARK OFFICE
CERTIFICATE OF CORRECTION

PATENT NO. : 9,818,283 B2
APPLICATION NO. : 14/589914
DATED : November 14, 2017
INVENTOR(S) : Ohad Akiva et al.

It is certified that error appears in the above-identified patent and that said Letters Patent is hereby corrected as shown below:

On the Title Page

In the Applicant section, item (71) correct "Harman International Industries, Incorporated, Stamford, CT (US)" to read "iOnRoad Technologies, Ltd., Ramat-Gan (IL)".

Signed and Sealed this
Twenty-third Day of January, 2018

Joseph Matal
*Performing the Functions and Duties of the*
*Under Secretary of Commerce for Intellectual Property and*
*Director of the United States Patent and Trademark Office*